United States Patent
Franz et al.

(10) Patent No.: US 11,481,301 B2
(45) Date of Patent: Oct. 25, 2022

(54) MEDICAL DEVICE ARRANGEMENT WITH A TEST MODULE

(71) Applicant: Drägerwerk AG & Co. KGaA, Lübeck (DE)

(72) Inventors: Frank Franz, Lübeck (DE); Stefan Schlichting, Lübeck (DE); Jasper Diesel, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 43 days.

(21) Appl. No.: 17/196,050

(22) Filed: Mar. 9, 2021

(65) Prior Publication Data

US 2021/0286696 A1 Sep. 16, 2021

(30) Foreign Application Priority Data

Mar. 10, 2020 (DE) .................. 10 2020 001 561.1

(51) Int. Cl.
| | | |
|---|---|---|
| *G06F 11/00* | (2006.01) | |
| *G06F 11/30* | (2006.01) | |
| *G06F 11/263* | (2006.01) | |
| *G06F 11/16* | (2006.01) | |
| *A61B 90/00* | (2016.01) | |

(52) U.S. Cl.
CPC ........ *G06F 11/3065* (2013.01); *A61B 90/361* (2016.02); *G06F 11/1641* (2013.01); *G06F 11/263* (2013.01)

(58) Field of Classification Search
CPC ..... G06F 11/3065; G06F 11/263; G06F 11/26
See application file for complete search history.

(56) References Cited

U.S. PATENT DOCUMENTS

| 6,035,657 | A | * | 3/2000 | Dobak, III | ............. F28F 13/06 62/50.7 |
| 2002/0121913 | A1 | * | 9/2002 | Miller | ................ G01R 31/2874 324/750.08 |
| 2007/0038039 | A1 | * | 2/2007 | Adler | .................... G06F 11/263 600/300 |
| 2009/0018407 | A1 | * | 1/2009 | Jung | ...................... A61B 3/113 705/2 |

(Continued)

FOREIGN PATENT DOCUMENTS

| DE | 102005037230 A1 | 2/2007 |
| DE | 102014212632 A1 | 12/2015 |

*Primary Examiner* — Amine Riad
(74) *Attorney, Agent, or Firm* — McGlew and Tuttle, P.C.

(57) ABSTRACT

A medical device arrangement (100) tests processing of data sets to be processed during operation of the medical device arrangement. The arrangement includes a data interface (110), analysis modules (120) and a test module (130). The analysis modules process a received medical data set (105). Each analysis module (122, 123, 124) forms a processing instance (390) for the medical data set or for the medical data set (125, 125') already preprocessed by at least one other analysis module. The test module outputs a test data set (132) to one of the analysis modules during operation such that this analysis module processes the test data set in the same manner as the medical data set. The test module compares a correspondingly outputted, processed test data set (134) with a reference result (136) associated with the test data set and determines a test result (137) based on this comparison.

20 Claims, 4 Drawing Sheets

(56) References Cited

U.S. PATENT DOCUMENTS

| | | | |
|---|---|---|---|
| 2010/0332904 A1* | 12/2010 | Bloching | G06F 11/2294 |
| | | | 714/E11.159 |
| 2013/0086573 A1* | 4/2013 | Moritzen | G06F 8/65 |
| | | | 717/171 |
| 2015/0019706 A1* | 1/2015 | Raghunathan | G06F 11/3664 |
| | | | 709/224 |
| 2017/0103524 A1 | 4/2017 | Franz et al. | |

\* cited by examiner

MEDICAL DEVICE ARRANGEMENT WITH A TEST MODULE

CROSS REFERENCE TO RELATED APPLICATIONS

This application claims the benefit of priority under 35 U.S.C. § 119 of German Application 10 2020 001 561.1, filed Mar. 10, 2020, the entire contents of which are incorporated herein by reference.

TECHNICAL FIELD

The present invention pertains to a medical device arrangement with a test module for testing the processing of data sets to be processed during the operation of the medical device arrangement. The present invention pertains, furthermore, to a process for testing the processing of data sets to be processed during the operation of a medical device arrangement.

TECHNICAL BACKGROUND

It is known that for testing the ability of components of an electronic device arrangement to function, such a component is actively polled for status information and/or status information is passively obtained from such a component during the operation. A failure of this component shall be able to be detected and corresponding problems shall be able to be corrected hereby as rapidly as possible. This is especially advantageous for safety-relevant applications, in which a failure or a malfunction of a component has an effect, for example, on the health of the user of the device arrangement.

In order to increase the reliability of such device arrangements or device systems, for example, 1oo2, 2oo2 or 2oo3 architectures are used in practice. Here, "oo" means, spelled out, "out of." Thus, two independent hardware channels, which can come to the same result independently in themselves, are embodied in the 1oo2 architecture. As a result, the system is still able to function in case of a failure of one hardware channel. It is required in the 2oo2 architecture that both hardware channels come to a consistent result in order to achieve a result tested hereby. In a 2oo3 architecture, there are three independent hardware channels, two of which must show a consistent result in order to come to a result tested hereby.

SUMMARY

An object of the present invention is to provide an improved testing of the processing of data sets to be processed, in particular an especially reliable testing of the processing of these data sets during the operation of a medical device arrangement.

A medical device arrangement with a test module for testing the processing of data sets to be processed during the operation of the medical device arrangement, having a data interface, a number of analysis modules and the test module, is proposed according to the present invention for accomplishing this object.

The data interface is configured to receive a medical data set to be processed. The data interface may be according to the present invention an interface of a cable-based or wireless connection. The configuration of such a data interface is known for a plurality of possible connections and will not be explained in detail below.

The number of analysis modules is configured to process the medical data set, wherein each analysis module forms a processing instance for the medical data set or for the medical data set already preprocessed by at least one analysis module, and wherein the medical data set is outputted as an output data set after the processing by the number of analysis modules. The analysis modules may be components of a common analysis, which are separated in space, or at least partially different software blocks of a single component for providing this joint analysis.

The test module is configured to output a test data set to at least one analysis module, especially to one analysis module of the number of analysis modules during the operation of the medical device arrangement such that this analysis module processes the test data set in the same manner as it does the medical data set. The test module is configured, furthermore, to compare, after a processing of the test data set by the analysis module or by a plurality of consecutive analysis modules, a correspondingly outputted, processed test data set with a reference result associated with the test data set and to determine a test result based on this comparison. Finally, the test module is further configured to output corresponding warning information in case of an insufficient agreement between the processed test data set and the associated reference result. The output of the warning function may take place, for example, internally to an additional module of the medical device arrangement and/or to an external module outside the medical device arrangement and/or to a user. The associated reference result is typically the result that the analysis modules would output without the presence of a malfunction during the processing of the test data set.

It was found within the framework of the present invention that the operability of the analysis modules used can be achieved during an operation of the medical device arrangement in an especially simple manner by the processing of data by the analysis modules being reconstructed on the basis of test data with a corresponding, associated reference result. A test module is provided according to the present invention in the medical device arrangement for introducing these test data and for comparison of the test data with the associated reference result.

The use of test data sets makes it advantageously possible to test different sources of fault within the number of analysis modules. Thus, even especially complex and/or fault-prone scenarios can be depicted for medical data as a test on the basis of the test data set. Furthermore, especially many different scenarios for medical data can be depicted as a test by the use of test data sets. This makes possible an especially reliable testing of the operability of the medical device arrangement during the operation.

The medical device arrangement according to the present invention makes it advantageously possible to detect a malfunction, which has not been present when the arrangement was made available, for example, in the presence of corrupted hardware in the form of bit flips, which may have been caused by cosmic radiation or by an interruption of the power supply. The medical device arrangement according to the present invention is therefore especially advantageous compared to prior-art test processes, in which different test scenarios outside a regular operation are tested prior to the medical device arrangement being made available.

Thus, the testing according to the present invention is especially advantageous in the case of the occurrence of random faults, which do not occur in a reproducible manner. While systematic, reproducible faults are typically detected already prior to the delivery of the medical device arrangement to the end user, random faults may also occur when a product was designed and tested in an incorrect manner. Such random faults, which may occur during the operation, are detected by the medical device arrangement according to the present invention after a certain time, so that their presence will not remain undetected for a needlessly long time. The medical device arrangement according to the present invention makes it possible in this sense to achieve in an especially advantageous manner a so-called "single fault safety," as it is described in IEC 60601-1.

The different components of the medical device arrangement according to the present invention may be contained in a single, common housing or in a plurality of housings, partially separated from one another.

The number of analysis components (analysis modules) and the test module are preferably parts of a processing by a common processor or by a plurality of processors, which parts are separated in the test module at the software level. The one or more processors may be associated with memory or a memory unit.

The criteria as to the point starting from which an agreement of parts of two data sets leads in a direct comparison to a sufficient agreement in the sense of the present invention are preferably stored in a memory of the test module and are applied by the test module to determine the test result.

The medical device arrangement is an arrangement of data-processing components, which has an information exchange with at least one data-logging medical device. The medical device arrangement may thus be arranged directly at or in the medical device or form a component separated in space from the at least one data-logging medical device or form a plurality of components separated in space from the at least one data-logging medical device.

Preferred embodiments of the medical device arrangement according to the present invention will be described below.

In a preferred embodiment, the test module is further configured to provide corresponding test information in case of a sufficient agreement between the processed test data set and the associated reference result. In this embodiment, corresponding information pertaining to the testing carried out and the corresponding test result are stored in case of a sufficient agreement and in case of an insufficient agreement. As a result, a user of the medical device arrangement is able to reconstruct, even after a certain time period, which analysis modules were tested and in what manner during the certain time period in question.

In a preferred embodiment, the test module has, furthermore, a memory and is configured to obtain from the memory the reference result associated with the test data set as a test data pair from a predefined plurality of test data pairs. The data sets that belong together can be accessed in an especially simple manner in this embodiment. The test data set and the reference result preferably have a common identification, which ensures during an electronic analysis that the association of the test data set and the reference data set is always possible.

In an especially preferred embodiment, the test data sets from the predefined plurality of test data pairs are predefined such that the largest possible number of different result states of the respective analysis module are produced by the test data set.

In an especially advantageous embodiment, the assignment from the processed test data set to the associated reference result takes place via a common test number and/or test digit. Such a test number and/or test digit can ensure that it is still recognizable even after a performed processing and/or after a certain further run time of the medical device arrangement that the processed data set was originally the test data set associated with the reference result. This is especially advantageous if a plurality of test data sets are processed simultaneously. As an alternative or in addition, it can be recognized on the basis of the test number and/or the test digit whether an incorrect change of the test data set or of the associated reference result has taken place. Furthermore, the test number of a test data set can be used to test a processing of a test data set on the basis of a test sum of test numbers, for example, of the test data set and the associated reference result or of a plurality of test data sets. A comparison of a result calculated for the test data set with the reference result can also be carried out on the basis of test numbers and/or test digits.

In another advantageous embodiment, a respective test sum is associated with the respective test data set. The respective analysis module or the test module is configured to test prior to a processing of the corresponding test data set based on the test sum whether the test data set to be processed, which is provided by the test module, is also the originally stored test data set. It can be avoided hereby that a corrupted test data set leads to an incorrect output of warning information, because faults within the test data set can be detected in time. The precise association of a suitable test sum is known to the person skilled in the art, so that concrete processes for determining a test sum will not be explained below. The association of the processed test data set with the reference result may advantageously also be carried out on the basis of the test sum of the test data set.

In an especially advantageous embodiment, a respective analysis module is configured to provide for the processing of a test data set to be processed a processing instance which is parallel to the processing instance for the medical data set and which processes the test data set in the same manner as the respective analysis module processes the medical data set. The processing of the medical data during the operation of the medical device arrangement is not interrupted or substantially interfered with by the testing by means of the test data set in this embodiment. The parallel processing instance is, for example, a copy of a software block, which forms the original processing instance of the respective analysis module. As an alternative, the parallel processing instance may be an instance of a programmed object class. The provision of a parallel processing instance at the software level advantageously reduces manufacturing costs compared to a parallel processing instance that is provided at the hardware level as a fixed, i.e., static processing instance. In a preferred variant, there is a respective parallel processing instance only for an analysis module or for individual analysis modules of the plurality of analysis modules. Costs can be reduced hereby compared to the provision of parallel processing instances for all analysis modules.

In a preferred variant of the above embodiment, the test module is further configured to output the test data set to be processed to both the processing instance and the parallel processing instance and to determine a first test result for the processing instance and a second test result for the parallel processing instance. By testing both processing instances in this variant, it is possible to check whether the processing instance used up to this point is operating correctly. Testing the parallel processing instance shows only whether the copy of the processing instance is operating, so that any possible faults during the copying of the processing instance would not make it conclusively possible to make a reliable statement on the operability of the original processing instance. Furthermore, the testing of the processing instance used up to that point makes it possible to validate data used up to that point. In an alternative embodiment, different test data sets to be processed are outputted to the processing instance and to the parallel processing instance, and a first test result is determined for the first processing instance and a second test result is determined for the parallel processing instance.

In another advantageous embodiment, the parallel processing instance is used as the processing instance to be used for the medical data in case of a sufficient agreement between the processed test data set and the associated reference result. It is ensured in this embodiment that the processing instance used after the testing has led to a sufficient agreement between the processed test data set and the associated reference result. The processing instance originally used for the processing of the medical data set is preferably deleted.

In another embodiment, a parallel processing graph is provided by a plurality of analysis modules of the number of analysis modules, and the test data set is processed in this parallel processing graph in the same manner in which the plurality of analysis modules as a chain of processing instances process the medical data set. As was described in the above embodiments, a test data set is also fed to the original processing graph in one variant besides to the parallel processing graph, and a respective test result is determined for both graphs. And the original processing graph is discarded in case of an agreement detected on the parallel processing graph. In addition, the data sets calculated up to that point can be considered to be validated.

In an especially preferred embodiment of the medical device arrangement according to the present invention, the test module is configured to determine the analysis module to be tested, a test time to be used for the testing and/or the test data set to be outputted at least partially via a randomized process. It is ensured by such a randomized determination that parts of the analysis module or subsets of possible medical data sets are not taken systematically into account by the test module during the testing. Furthermore, it is ensured that a large number of different scenarios can be modulated on the basis of the test data sets used by the test module. As a result, it is possible randomly to detect even difficult-to-detect faults within the number of analysis modules, without these faults being relevant for the processing of usual, medical data. It can thus be ensured that a fault-free processing is provided by the number of analysis modules even for medical data sets having an unusual content.

In one embodiment, which is an alternative or addition to the previous embodiment, the medical device arrangement has, furthermore, a security module, which is configured to output a start signal in case of a faulty behavior of the number of analysis modules, which start signal indicates the presence of the faulty behavior, and wherein the test module is further configured to receive the start signal and to at least partially determine, depending on the start signal, the analysis module to be tested, a test time to be used for the testing and/or the test data set to be outputted. For example, the security module may send an automated polling of status signals and receive in response corresponding status signals. The absence of such a receipt of status signals can be detected as a faulty behavior and lead to the output of the start signal. Furthermore, a faulty behavior can be detected if the output data set or an individual processed data set can be associated with a data set type from a predefined group of obviously incorrect data set types. This predefined group of obviously incorrect data set types may have, for example, one of the following elements: A stream of identical data lasting over the predefined time period, data sets of non-stored test numbers and/or test digits, data sets with empty data elements, data set sequences with a data rate below a predefined rate threshold value, data sets with a signal-to-noise ratio below a predefined ratio threshold value and/or a data set with unknown data structure. In another variant, a faulty behavior is detected by a separate sensor, e.g., an acceleration sensor and/or an optical sensor of the medical device arrangement.

In another embodiment, the medical device arrangement has a sensor unit, which is configured to determine medical data and to determine the medical data set based on the medical data and to output it via the data interface to the number of analysis modules. The sensor unit typically records medical data concerning a patient by a corresponding sensor element in this embodiment. The assessment of whether a sufficient agreement is present between the processed data set and the associated reference result typically depends on the type of the sensor elements used within the sensor unit. In an advantageous variant of this embodiment, the absence of warning information leads to a recalibration of the sensor unit recording the medical data.

In an especially preferred embodiment, the test module and/or the respective analysis module are configured to provide a predefined temporary fault state of the analysis module in order to be able to detect a malfunction of the test module. A faulty behavior of the test module is detected in this embodiment by testing whether the fault of an analysis module, which fault is present due to the predefined temporary fault state, is also actually detected by the test module. A fault of the test module may lead, for example, to the provision of a fault output, especially of a fault output for a user of the medical device arrangement.

In an especially advantageous embodiment, the test module has a plurality of processing instances, which are configured to check the presence of a sufficient agreement between a processed test data set and the associated reference result. The different processing instances preferably operate with different algorithms during the determination of the sufficient agreement. The results of the plurality of processing units are especially advantageously compared and, for example, a sufficient agreement is determined if the plurality of processing units have determined a sufficient agreement. Especially reliable is a variant of this embodiment in which a sufficient agreement is determined only if all processing units of the plurality of processing units have determined a sufficient agreement.

In a preferred embodiment, the medical device arrangement comprises an optical monitoring system for monitoring the environment of a patient. The medical device arrangement of the invention may advantageously comprises features as disclosed in US 2017-0103524 A1. US 2017-0103524 A1 is incorporated herein by reference. The optical monitoring system preferably operates in an automated manner, so that a testing according to the present invention of the processing of data sets to be processed can especially advantageously find a fault in a processing process that can otherwise only be tested with difficulty. According to the present invention, the first analysis module of the plurality of analysis modules is, for example, the analysis module that generates an information technology representation from received sensor data from an optical sensor.

In an especially preferred variant of the above embodiment, the test data set to be processed indicates predefined image information. The reference result associated with the test data set indicates a fact represented within the predefined image information. Unusual image information may especially advantageously be used in this variant in order to make possible a fault-free operation of the optical monitoring system even in such a special case.

The security module of the medical device arrangement may especially advantageously be configured to detect a faulty behavior of an analysis module during the processing of optical sensor data by the output data set or an individual processed data set being able to be associated with a data set type from the predefined group of obviously incorrect data set types. The group of obviously incorrect data set types comprises here at least one of the following incorrect data set types: A predefined number of invalid pixels within a data set indicating an image, a sequence of essentially identical image data within a data set indicating an image sequence, a lower data rate within a data set indicating an image sequence, a signal-to-noise ratio below a predefined limit value, and an absence of identification features of an image area to be investigated within a data set indicating an image. The absence of identification features may point, for example, to the circumstance that a currently observed area of an optical sensor array does not correspond to the area to be observed. In an advantageous variant, the faulty behavior is detected by an additional sensor of the medical device arrangement and it triggers thereby a testing by the test module. The additional sensor may be, for example, an acceleration sensor or an optical sensor. The acceleration sensor may indicate, for example, a rotation or a shifting of the sensor detecting the medical data. Furthermore, the optical sensor and/or image data may be used in order to detect a shifting or rotation of the sensor detecting the medical data by a comparison of the recorded image areas in past and current data sets, for example, by checking the presence of predefined identification points, for example, of a bed frame of a patient. The identification points may be both static objects, for example, a wall or a marking on a floor, as well as dynamically determined points within image data of a plurality of sensors, from which features concerning the calibration of the plurality of sensors are obtained.

It is preferably checked before the detection that the processed data set can be associated with a data set type from the predefined group of obviously incorrect data set types whether a part of an image area to be monitored is located within an image area to be monitored by the optical sensor under a minimum. If the minimum is not reached, a faulty behavior is detected, because this indicates a change in space of the optical sensor.

In addition or as an alternative to the above embodiments pertaining to the security module, an external security unit may be provided according to the present invention, which is not a part of the medical device arrangement, but it checks the processed data sets of the analysis modules and/or the output data set in exactly the same way as does the security module in the corresponding previous embodiments. The medical device arrangement according to the present invention is configured here such that the test module can receive a corresponding fault signal of the external security unit and start a corresponding testing of one or more analysis modules.

In another embodiment, at least one analysis module of the number of analysis modules is configured to detect an internal fault state and to trigger a testing of the corresponding analysis module by the test module in case of such a detection. The test module supports hereby the internal fault detection. If there was a fault during the detection of an internal fault state, this is detected by the test module according to the present invention.

In a preferred embodiment of the medical device arrangement according to the present invention, data interfaces, the number of analysis modules and the test module are arranged in a common housing. The number of analysis modules and the test module are preferably software components here within a processing unit, for example, a processor. In an alternative embodiment, the test module and/or at least one analysis module of the number of analysis modules are arranged in at least one separate housing.

According to another aspect of the present invention, a process for testing the processing of data sets to be processed during the operation of a medical device arrangement is proposed to accomplish the above object. The process according to the present invention has the following steps:
  receipt of medical data sets to be processed;
  processing of the medical data set by a number of analysis modules, wherein each analysis module forms a processing instance for the medical data set or for the medical data set already preprocessed by at least one other analysis module;
  outputting of a test data set to at least one analysis module of the number of analysis modules during the operation of the medical device arrangement;
  processing of the test data set in the same manner in which the medical data set is processed by one or more consecutive analysis modules and outputting of a corresponding processed test data set;
  comparison of an outputted processed test data set with a reference result associated with the test data set;
  determination of a test result based on the comparison; and
  outputting of corresponding warning information in case of an insufficient agreement between the processed test data set and the associated reference result.

The process according to the second aspect of the present invention has all the advantages that were already mentioned in connection with the medical device arrangement according to the present invention.

In particular, the process according to the present invention makes it also possible to detect faults within an analysis module, which were not yet present at the time at which the medical device arrangement was put into operation. An especially reliable medical device arrangement can thus be provided. The safety of a patient being treated by the medical device arrangement can be improved hereby.

The individual process steps can be carried out according to the present invention by a single processing unit, e.g., a processor, or, as an alternative, by a plurality of processing units, e.g., a plurality of processors. A software component can be associated within the processing unit with each processing step. Parts of the medical device arrangement, e.g., a processor of the medical device arrangement, may be arranged separated in space from additional parts of the medical device arrangement. In particular, the test module may be arranged separated in space from the number of analysis modules.

The present invention will be explained in more detail below on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying

DESCRIPTION OF PREFERRED EMBODIMENTS

Figure 1:
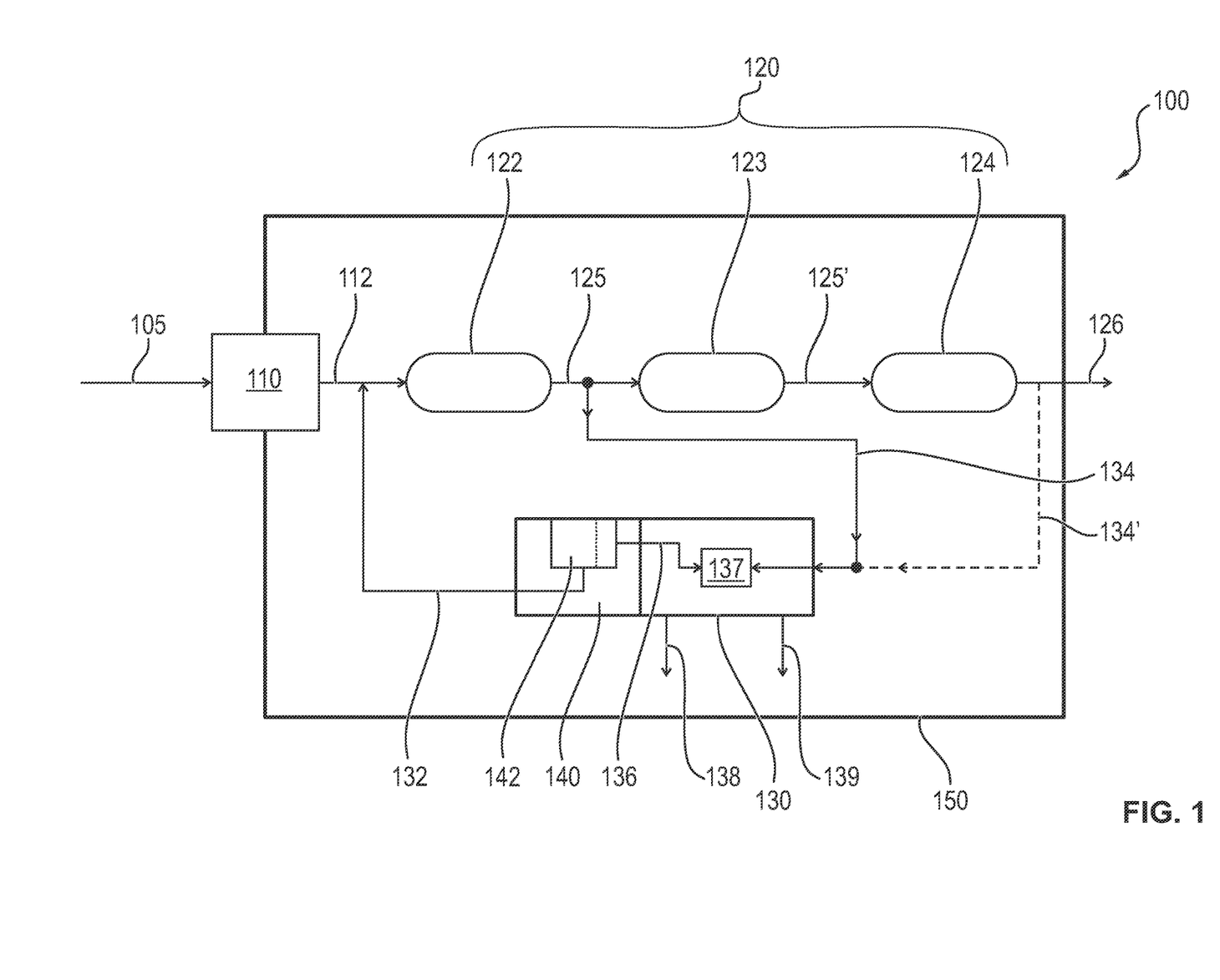
FIG. 1 is a schematic view showing a first exemplary embodiment of a medical device arrangement according to the present invention.

Referring to the drawings, FIG. 1 shows a schematic view of a first exemplary embodiment of a medical device arrangement 100 according to the present invention.

The medical device arrangement 100 has a data interface 110 and a number of analysis modules 120 as well as a test module 130 for testing the processing of medical data sets 105 to be processed during the operation of the medical device arrangement 100. The analysis modules 120 and the test module are preferably parts of a processing unit comprising a common processor or by a plurality of processors. These modules may be parts that are separated at a software level. The one or more processors are associated with a memory.

The data interface 110 is configured to receive the medical data set 105 to be processed. The connection between an external medical equipment, not shown, and the medical device arrangement 100 is a cable-based connection in the exemplary embodiment shown. In one exemplary embodiment, not shown, there is a wireless connection. In addition to the medical equipment, which may comprise a plurality of medical devices, a sensor unit may also have a connection to the medical device arrangement according to the present invention. The structure of such a data interface 110 is known to the person skilled in the art for all prior-art connection types and it will not therefore be explained below. The data interface 110 outputs an input signal 112, which contains the medical data set 105 to be processed in a form readable for at least one analysis module 122 of the number of analysis modules 120.

The number of analysis modules 120 are configured to process the medical data set 105 from the input signal 112, wherein each analysis module 122, 123, 124 forms a processing instance for the medical data set 105 or for the medical data set 125, 125' already preprocessed by at least one other analysis module 122, 123. All the analysis modules 122, 123, 124 are arranged as a linear analysis module graph in the exemplary embodiment shown. A partial parallel arrangement is shown in the exemplary embodiment shown in FIG. 2. The structure shown in FIG. 1 represents a simplification of a typically more complex arrangement of analysis modules for processing received data sets. An analysis module is, for example, a software block, which can be associated with the functions of the concrete analysis module, the processing within different analysis modules being preferably carried out by a single processor. Furthermore, the medical data set 105 is outputted after the processing by the number of analysis modules 120 as an output data set 126. The output data set is then sent to an additional device, for example, to an output unit, to a network, especially to a hospital network, or to another external device.

The test module 130 according to the present invention is configured to output a test data set 132 to an analysis module 122 of the number of analysis modules 120 during the operation of the medical device arrangement 100 such that this analysis module 120 processes the test data set 132 in the same manner as the medical data set 105, and wherein the test module 130 is configured, furthermore, to compare, following a processing of the test data set 132 by the analysis module 122 or by a plurality of consecutive analysis modules 122, 123, 124, a correspondingly outputted, processed test data set 134 to a reference result 136 associated with the test data set 132, and to determine a test result 137 on the basis of this comparison. The test module 130 is further configured to output corresponding warning information 138 in case of an insufficient agreement between the processed test data set 134 and the associated reference result 136. In the exemplary embodiment shown, the warning information 138 is outputted to an output unit, not shown. In an alternative or additional exemplary embodiment, not shown, the warning information is outputted to a processor by which the faulty analysis module is configured in order to trigger a fault corrective action within the processor. In the exemplary embodiment being shown, the test data set 132 is outputted to the first analysis module 122 of the shown sequence of analysis modules 122, 123, 124. A corresponding test data set can be provided according to the present invention for each of the analysis modules. The selection of the test data set within the test module preferably depends on the analysis module to be tested. In the exemplary embodiment being shown, the test module 130 has a memory 140, in which a predefined plurality of test data pairs 142 are stored. The predefined plurality have a respective plurality of test data pairs for a respective analysis module 122, 123, 124. The processed test data set 134 is taken in the exemplary embodiment shown directly behind the first analysis module 122 from the shown sequence of analysis modules 122, 123, 124 in order to carry out the comparison with the predefined associated reference result 136. The possible reading of the processed test data set 134' behind the complete sequence of analysis modules 122, 123, 124 is indicated by broken lines. Depending on which analysis modules the test data set 132 is processed by, a corresponding reference result 136 was assigned and stored in the memory 140. In one exemplary embodiment, which is shown, reading, not shown, of the processed test data set is also possible behind the analysis module 123.

The decision of the test module 130 as to which analysis module shall be tested by a test data set and/or which test data set is used for the testing and/or at what time the analysis module will be tested is determined in one exemplary embodiment, which is shown, on the basis of a randomized process. Examples of randomized processes are known to the person skilled in the art and will not therefore be explained below.

A criteria catalog stored in the memory 140 is preferably used to determine whether there is a sufficient agreement between the processed data set 134 and the associated reference result 136. For example, a maximum number of non-agreeing data points, at which a sufficient agreement is nevertheless determined, is stored in the criteria catalog. A version of the criteria catalog used is typically also stored permanently with the test result 137, so that a user can also recognize retrospectively after what criteria a comparison led to a sufficient agreement.

The test result is preferably indicated by the warning information 138 or by the test information 139. By storing these respective pieces of information, the test result can be stored permanently within the medical device arrangement or outside the medical device arrangement.

In case of a sufficient agreement between the processed test data set 134 and the associated reference result 136, corresponding test information 139 is stored in a separate memory, not shown, in the exemplary embodiment shown. It can be retrospectively recognized hereby which analysis module was tested and for which properties it was tested.

The test data pair stored in the memory 140 preferably comprises an association of a test data set with a reference result after the first analysis unit 122 and with a reference result after the second analysis unit 123 as well as with a reference result after the third analysis unit 124. Thus, depending on the information on which analysis module or what number of analysis modules were tested with which test data set, a corresponding test data pair is taken from such a test data group formed by the test data set. The reference results associated with a test data set and the corresponding test data set are preferably provided with a common test number and/or with a common test digit. As a result, it can be detected with certainty which test data set the processed test data set is associated with, and a fault within the test data set, for example, at a time when it is provided, can be detected on the basis of a change in the test number and/or the test digit.

The medical device arrangement 100 is arranged in a common housing 150. In other exemplary embodiments, individual components or groups of components are arranged in a separate housing.

Figure 2:
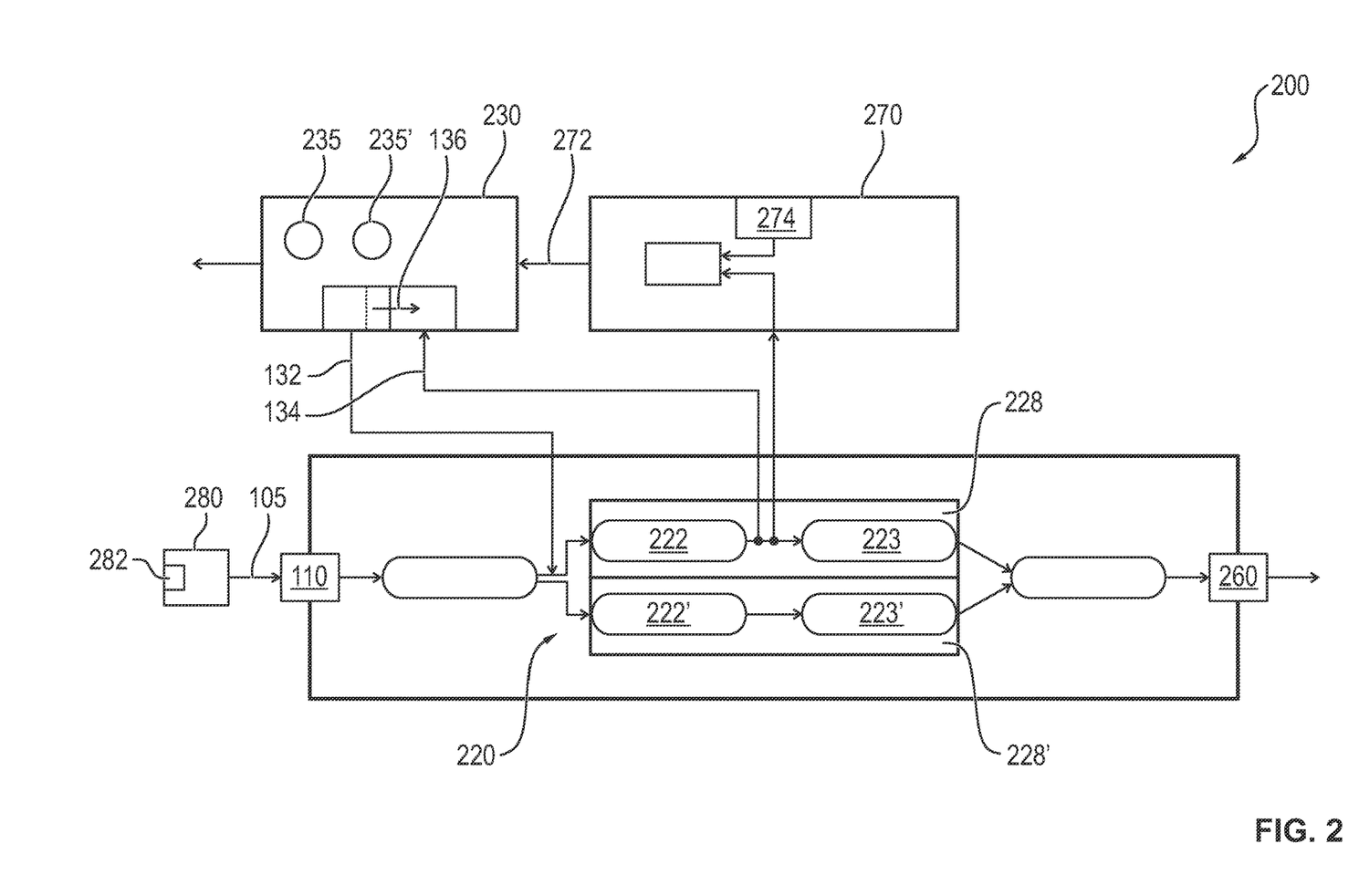
FIG. 2 is a schematic view showing a second exemplary embodiment of a medical device arrangement according to the present invention.

FIG. 2 shows a schematic view of a second exemplary embodiment of a medical device arrangement 200 according to the present invention.

The medical device arrangement 200 differs from the medical device arrangement 100 shown in FIG. 1, among other things, in that the structure of the analysis modules 220 has an area of analysis modules 222, 223, 222', 223' arranged in parallel to one another, so that there are two different analysis module graphs between the data interface 110 and an output interface 260. The mutually parallel analysis modules 222, 223, 222', 223' are configured on different processors 228, 228' in the exemplary embodiment shown. The other analysis modules are configured on a common processor.

In the exemplary embodiment shown, the test data set 132 is made available to the analysis module 222 and is removed directly behind the analysis module 222 as a processed test data set 134 in order to compare it to the associated reference result 136.

Furthermore, the medical device arrangement 200 differs from that shown in FIG. 1 in that it has, furthermore, a security module 270, which is configured to output a start signal 272, which indicates the presence of the faulty behavior, in case of a faulty behavior of the number of analysis modules 220. In the exemplary embodiment shown, an output of the analysis module 222 is tested by the security module 270. Such a test is carried out by testing whether the data set at the output can be associated with a data set type from a predefined group of obviously incorrect data set types. The group of obviously incorrect data set types is stored in an additional memory 274 of the security module 270 and contains at least one of the following incorrect data set types: A predefined number of invalid pixels within a data set indicating an image, a sequence of essentially identical image data within a data set indicating an image sequence, a lower data rate within a data set indicating an image sequence compared to a threshold value, a signal-to-noise ratio below a predefined limit value, and the absence of identification features of an image area to be investigated within a data set indicating an image. Furthermore, the security module 270 is preferably configured to check whether a part of an image area to be investigated within the investigated image area is above a predefined limit value. Should the part be smaller, this indicates an unintended change in space of the sensor unit being used. The security module 270 therefore also outputs the start signal 272 if the part of an image area to be investigated within the investigated image area is below the predefined limit value.

This group of obviously incorrect data set types arises in part from the sensor unit 280 of the medical device arrangement 200, which sensor unit 280 is used in this exemplary embodiment, and which has a number of optical sensors 282 such that the medical device arrangement has an optical monitoring system for monitoring the environment of a patient. The medical data set 105 to be processed therefore indicates image information as detected medical data. The test data set 132 to be processed thus likewise indicates predefined image information.

The test module 230 is additionally configured, furthermore, to receive the start signal 272 and, depending on the determined faulty behavior, to determine the corresponding analysis module 222 to be tested and/or to set a test time and/or to determine the test data set to be outputted at least partially. The triggering of the test by the start signal 272 is only a supplementary criterion along with a randomized selection of the test time, test data set and/or analysis module to be tested for the test module 230 in the exemplary embodiment shown.

Furthermore, the test module 230 has two processing units 235, 235', which are configured each to check the presence of a sufficient agreement between processed test data set 134 and reference result 136. In the exemplary embodiment shown, the presence of a sufficient agreement is determined as a test result only if both processing units 235, 235' arrive at this result.

In one exemplary embodiment, not shown, the test module has more than two such processing units, and a sufficient agreement is only determined if the majority of the processing units arrive at this result.

In another exemplary embodiment, not shown, the security module is configured only to detect a faulty behavior on the basis of a fault during the exchange of status information with one or more analysis modules. In another exemplary embodiment, not shown, an external security unit is provided, in addition or as an alternative to the security module, outside the medical device arrangement, and this security module is configured to detect a faulty behavior of one or more analysis modules by testing exchanged data sets and thereby to trigger a corresponding testing by the test module according to the present invention.

In the exemplary embodiment shown, the medical device arrangement 200 comprises three different housings, namely, one for the number of analysis modules 220, one for the test module 230 and one housing for the security module 270. In the exemplary embodiment shown, the transmission of data sets, especially of test data sets, may take place in a cable-based or wireless manner. In particular, the test module 230 and/or the security module 270 may be arranged separated in space from the number of analysis modules 220, specifically especially in another room.

In one exemplary embodiment, not shown, the test module, the security module and/or the respective analysis module are configured to provide a predefined, temporary fault state of the analysis module in order to be thereby able to detect a malfunction of the test module. It can thus be tested whether an intentional incorrect processing of the test data set by the analysis module is also detected as incorrect processing.

The transmission of data between components of the medical device arrangement according to the present invention may always take place, in principle, in a cable-based or wireless manner, the concrete technical implementation of such a connection being known to the person skilled in the art, and it will not therefore be explained in detail.

Figure 3:
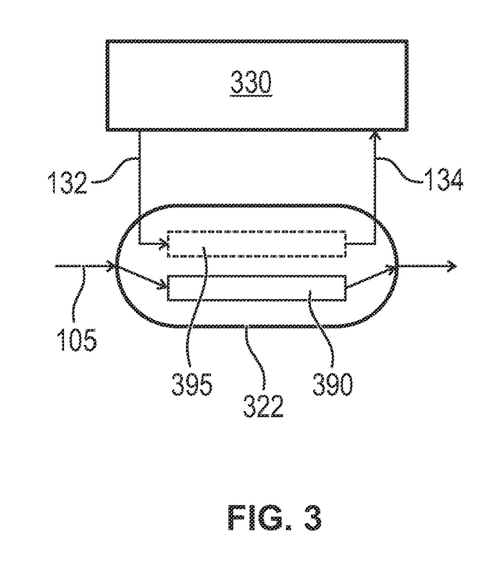
FIGS. 3, 4 and 5 are schematic views showing a processing of a medical data set and of a test data set by an analysis module according to an exemplary embodiment of the medical device arrangement according to the present invention, wherein the procedure is illustrated with respect to the provision of a parallel processing instance by the analysis module.
Figure 4:
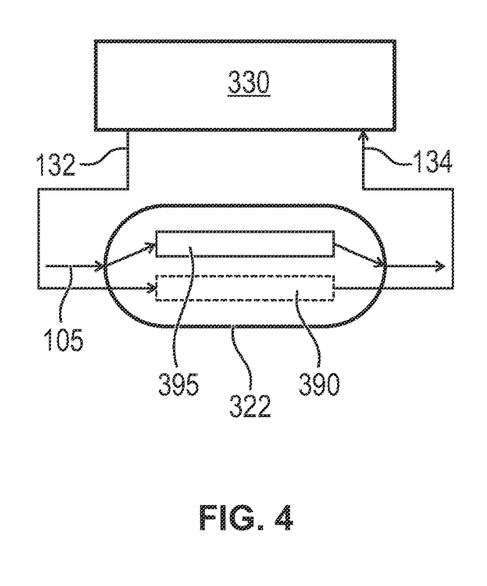
Figure 5:
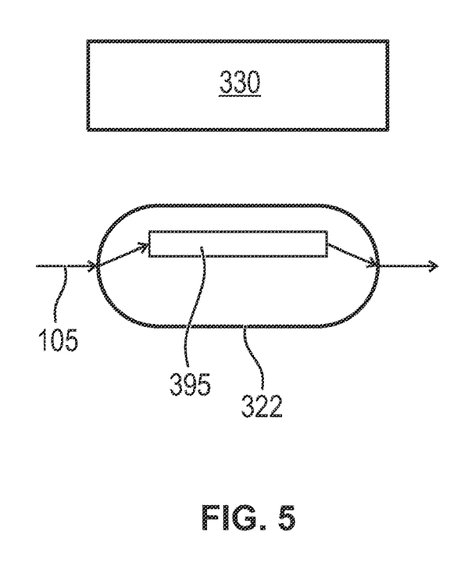

FIGS. 3, 4 and 5 show a schematic view of a processing of a medical data set 105 and of a test data set 132 by an analysis module 322 of an exemplary embodiment of the medical device arrangement according to the present invention, wherein the procedure related to the provision of a parallel processing instance 395 by the analysis module 322 is illustrated.

It is shown in FIG. 3 that in addition to the processing instance 390 of the analysis module 322, which processing instance 390 processes the medical data set 105, the analysis module 322 generates a parallel processing instance 395 within the analysis module 322 for processing the test data set 132 provided by the test module 330. The parallel processing instance 395 may be, for example, a copy of a software block of the processing instance 390, which was generated for processing the test data set 132 parallel to the further processing of the medical data set 105 via the processing instance 390. As an alternative to the copy, a corresponding additional instance of a programmed object class may be used to provide the parallel processing instance.

As was described in the above exemplary embodiments, the analysis module 322 compares the process test data set 134 to an associated reference result and checks thereby whether the parallel processing instance 395 processes the test data set 132 in a fault-free manner. The parallel processing instance 395 processes here an incoming data set in the same manner in which the processing instance 390 processes the medical data set 105.

If the comparison between the processed test data set 134 and the associated reference result shows a sufficient agreement, the parallel processing instance 395 becomes the processing instance that is the current processing instance starting from the test time for the processing of the medical data set 105. This switching of the processing instance responsible for the processing of the medical data set is shown in FIG. 4.

In the exemplary embodiment shown, the processing instance 390 used originally is tested within the analysis module 322 after switching the relevant processing instance. A test data set 132 of this originally used processing instance 390 is thus again made available and the processed test data set 134 is compared to an associated reference result. If a sufficient agreement is determined, it is inferred from this that data sets processed by the processing instance 390 used originally were processed fault-free. The processing instance 300 used originally is then discarded as a result and the new, originally parallel processing instance 395 becomes the only processing instance within the analysis module 322, as is shown in FIG. 5.

If the testing of the originally used processing instance 390 shows that the processed data sets were processed incorrectly, corresponding warning information is preferably outputted. In an especially preferred variant of this exemplary embodiment, the originally parallel processing instance 395 is then tested again.

The simultaneous processing of the medical data set 105 in addition to the test data set 132 provided is advantageous in connection with the use of a parallel processing instance. In one exemplary embodiment, not shown, the medical data set and the test data set are processed in a common processing instance. A further output of the processed data set is interrupted for this purpose, for example, for a short period of preferably less than 20 sec, especially less than 10 sec, and especially preferably for less than 5 sec, so that the processed test data set has no effect on the output of the medical device arrangement. In a preferred variant of this exemplary embodiment, not shown, a new start state, which differs from the state currently used for the medical data set, is set for the processing of the test data set within the common processing instance. Should the testing by the test module lead to a sufficient agreement, the new start state becomes the state of the processing instance to be used for the medical data set, and the original state of the processing instance is discarded. It is not necessary in this variant, which is not shown, to be able to implement a plurality of processing instances simultaneously for the analysis module.

In another exemplary embodiment, not shown, the processing of the test data set is carried out by a new start state within the processing instance of the analysis module, which processing instance processes the medical data set to be processed. Parallel to the medical data set, the test data set can thus be processed without providing a parallel processing instance. Should the testing by the test module lead to a sufficient agreement, the new start state becomes the state of the processing instance to be used for the medical data set, whereas the original state of the processing instance, via which the medical data set was hitherto processed, is discarded. No interruption of the processing of the medical data set is advantageously necessary in this exemplary embodiment, not shown, for the processing of the test data set because a parallel processing of both data sets takes place within one instance.

In another exemplary embodiment, not shown, the parallel processing of the test data set to be processed and of the medical data set is carried out via two separate hardware components of an analysis module.

The testing by the test module according to the present invention can be combined, in principle, with other prior-art testing processes, especially with processes that check the plausibility of received data sets compared to earlier data sets.

Figure 6:
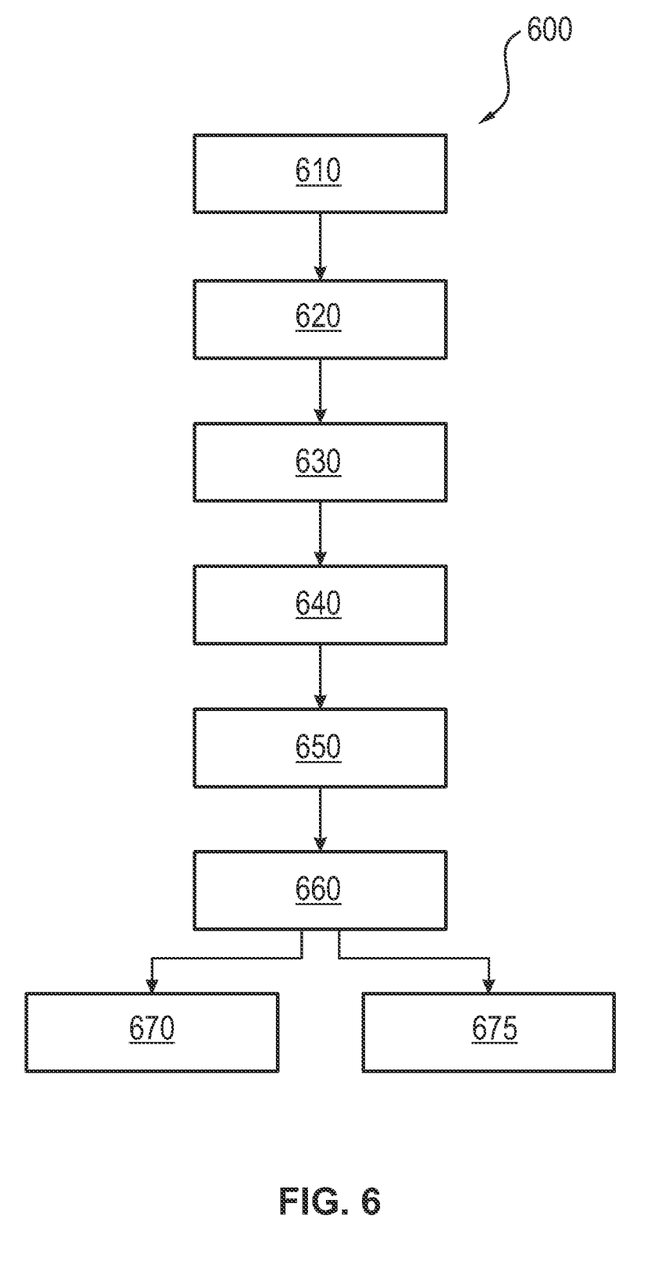
FIG. 6 is a flow chart of an exemplary embodiment of a process according to another aspect of the present invention.

FIG. 6 shows a flow chart of an exemplary embodiment of a process 600 according to another aspect of the present invention.

The process 600 according to the present invention is preferably used to check the processing of data sets to be processed during the operation of a medical device arrangement. It has the process steps explained below.

A first step 610 comprises the receipt of a medical data set to be processed.

A next step 620 comprises a processing of the medical data set by a number of analysis modules, wherein each analysis module forms a processing instance for the medical data set or for the medical data set already preprocessed by at least one other analysis module.

A next step 630 comprises the outputting of a test data set to an analysis module of the number of analysis modules during the operation of the medical device arrangement.

Another step 640 comprises a processing of the test data set in the same manner as the medical data set is processed by one or more consecutive analysis modules and an outputting of a corresponding processed test data set.

A next step 650 comprises a comparison of an outputted processed test data set with a reference result associated with the test data set.

A next step 660 comprises the determination of a test result based on the comparison.

A final step 670 comprises the outputting of corresponding warning information in case of an insufficient agreement between the processed test data set and the associated reference result.

In case of a sufficient agreement between the processed test data set and the associated reference result, a final step 675 that is an alternative to step 670 comprises the provision of corresponding test information.

Steps 610 and 620 describe a usual processing of a medical data set by the medical device arrangement. Steps 630 through 660 must be carried out in the order indicated and they describe the process according to the present invention for testing the operability of the number of analysis modules during the operation of the medical device arrangement. These steps are carried out in the same sequence in each testing process.

Steps 670 and 675 are two alternative steps, which describe the corresponding further procedure according to the present invention depending on the result of the testing. In case of an insufficient agreement, warning information is outputted according to the present invention, whereas test information is provided in especially preferred exemplary embodiment, such as in the exemplary embodiment described, even in the case of a sufficient agreement in order to make it possible to reconstruct the past times and contents of tests of an analysis module even retrospectively.

The time at which step 630 is carried out is preferably determined in a randomized manner, as it is described within the framework of previous exemplary embodiments.

A plurality of tests of an analysis module or of a plurality of analysis modules of the number of analysis modules may also take place in parallel according to the present invention. The process steps 630 through 660 according to the present invention must be carried out separately for each of this plurality of tests. The alternative final steps 670 and 675 are likewise outputted separately for each test in preferred exemplary embodiments. A plurality of test results, for example, test results located close to one another in time, on common warning information and/or on common corresponding test information, are combined within the framework of the final steps 670 and 675 in further exemplary embodiments.

While specific embodiments of the invention have been shown and described in detail to illustrate the application of the principles of the invention, it will be understood that the invention may be embodied otherwise without departing from such principles.

LIST OF REFERENCE NUMBERS

100, 200 Medical device arrangement
105 Medical data set
110 Data interface
112 Input signal
120, 220 Number of analysis modules
122, 123, 124, 222, 222', Analysis module
223, 223', 322
125, 125' Preprocessed medical data set
126 Output data set
130, 230, 330 Test module
132 Test data set to be processed
134 Processed test data set
136 Associated reference result
137 Test result
138 Warning signal
139 Test information
140 Memory
142 Test data pair
150 Housing
228, 228' Processor of the analysis unit
235, 235' Processing unit of the test module
260 Output interface
270 Security module
272 Start signal
274 Additional memory
280 Sensor unit
282 Number of optical sensors
390 Original processing instance
395 Parallel processing instance
600 Process
610, 620, 630, 640, 650, Process steps
660, 670, 675

What is claimed is:

1. A medical device arrangement comprising:
    a data interface configured to receive a medical data set to be processed;
    a number of analysis modules configured to process the medical data set, wherein:
        each of the analysis modules forms a processing instance for the received medical data set or for a preprocessed medical data set comprised of the received medical data set already preprocessed by at least one other of the analysis modules; and
        a processed medical data set is output after the processing by the number of analysis modules as an output data set; and
    a test module, the test module being configured:
        to output a test data set to one or more of the analysis modules, during the operation of the medical device arrangement, such that said one or more of the analysis modules processes the test data set in a manner corresponding to a processing of the medical data set by one or more of the analysis modules;
        to compare, after a processing of said at least the test data set by said at least one of the analysis modules or by a plurality of consecutive analysis modules including said at least one of the analysis modules, an output and processed test data set with a reference result associated with the test data set;
        to determine a test result based on the comparison; and
        to output corresponding warning information in case of an insufficient agreement between the output and processed test data set and the associated reference result.

2. A medical device arrangement in accordance with claim 1, wherein the test module is further configured to provide test information in case of an insufficient agreement between the processed test data set and the associated reference result.

3. A medical device arrangement in accordance with claim 1, wherein:
    the test module further comprises a memory; and the test module is configured to take the test data set and the reference result associated with the test data set as a test data pair from a predefined plurality of test data pairs from the memory.

4. A medical device arrangement in accordance with claim 1, wherein the association of the processed test data set with the associated reference result is carried out via a common test number or via a test sum of the test data set.

5. A medical device arrangement in accordance with claim 1, wherein respective analysis modules are configured to provide a parallel processing instance, that is parallel to the processing instance for the medical data set, for processing a test data set, which parallel processing instance processes the test data set as the processing instance for the medical data set processes the medical data set.

6. A medical device arrangement in accordance with claim 5, wherein the test module is further configured to output the test data set to be processed to both the processing instance and the parallel processing instance and to determine a first test result for the processing instance and a second test result for the parallel processing instance.

7. A medical device arrangement in accordance with claim 5, wherein the parallel processing instance is used as a processing instance to be used for the medical data set in case of a sufficient agreement between the processed test data set and the associated reference result.

8. A medical device arrangement in accordance with claim 1, wherein the test module is configured to determine one of the analysis modules that is to be tested, a test time to be used for the testing; and/or the test data set to be outputted, at least partially via a randomized process.

9. A medical device arrangement in accordance with claim 1, further comprising a security module configured to output, in case of a faulty behavior of the number of analysis modules, a start signal, which indicates a presence of the faulty behavior, and wherein the test module is further configured to receive the start signal and to determine at least partially the analysis modules to be tested, a test time to be used for the testing and/or the test data set to be outputted depending on the start signal.

10. A medical device arrangement in accordance with claim 1, further comprising a sensor unit configured to determine medical data and to determine the medical data set based on the medical data and to output the determined medical data and the determined medical data set to the number of analysis modules via the data interface.

11. A medical device arrangement in accordance with claim 1, wherein at least one of the test module and the respective analysis modules are configured to provide a predefined temporary fault state of the analysis module in order to be able to detect a malfunction of the test module.

12. A medical device arrangement in accordance with claim 1, wherein the test module comprises a plurality of processing instances, which are configured to check a presence of a sufficient agreement between a processed test data set and an associated reference result.

13. A medical device arrangement in accordance with claim 1, wherein the medical device arrangement comprises an optical monitoring system for monitoring a patient environment of a patient.

14. A medical device arrangement in accordance with claim 13, wherein the test data set to be processed indicates predefined image information.

15. A process for testing the processing of data sets to be processed during the operation of a medical device arrangement the process comprising the steps of:
receiving a medical data set to be processed;
processing the medical data set by a number of analysis modules, wherein each analysis module forms a processing instance for the received medical data set or for a preprocessed medical data set comprised of the received medical data set already preprocessed by at least one other of the analysis modules;
outputting a test data set to at least one analysis module of the number of analysis modules during operation of the medical device arrangement;
processing the test data set in a manner corresponding to a processing of the medical data set, by one or more of the analysis modules;
outputting a processed test data set;
comparing the processed test data set output with a reference result associated with the test data set;
determining a test result based on the comparison; and
outputting corresponding warning information in case of an insufficient agreement between the processed test data set and the associated reference result.

16. A process in accordance with claim 15, wherein a test module is configured to output the test data set and to provide test information in case of an insufficient agreement between the processed test data set and the associated reference result.

17. A process in accordance with claim 16, wherein the test module further comprises a memory and the test module takes the test data set and the reference result associated with the test data set as a test data pair from a predefined plurality of test data pairs from the memory.

18. A process in accordance with claim 15, wherein the association of the processed test data set with the associated reference result is carried out via a common test number or via a test sum of the test data set.

19. A process in accordance with claim 15, wherein:
respective analysis modules are configured to provide a parallel processing instance, that is parallel to the processing instance for the medical data set, for processing the test data set, which parallel processing instance processes the test data set as the respective analysis module processes the medical data set; and
a test module is configured to output the test data set to be processed, to both the processing instance and the parallel processing instance and to determine a first test result for the processing instance and a second test result for the parallel processing instance.

20. A process in accordance with claim 15, wherein a sensor unit is configured to determine medical data and to determine the medical data set based on the determined medical data and to output the determined medical data and the determined medical data set to the number of analysis modules via a data interface.

* * * * *